(12) United States Patent
Shelton

(10) Patent No.: US 8,025,629 B2
(45) Date of Patent: Sep. 27, 2011

(54) WIRE GUIDE TORQUE DEVICE

(75) Inventor: Jerry A. Shelton, Ararat, NC (US)

(73) Assignee: Cook Medical Technologies LLC, Bloomington (IN)

( * ) Notice: Subject to any disclaimer, the term of this patent is extended or adjusted under 35 U.S.C. 154(b) by 403 days.

(21) Appl. No.: 11/432,089

(22) Filed: May 11, 2006

(65) Prior Publication Data

US 2007/0004991 A1    Jan. 4, 2007

Related U.S. Application Data

(60) Provisional application No. 60/680,102, filed on May 12, 2005.

(51) Int. Cl.
*A61M 25/00* (2006.01)
*B25H 3/00* (2006.01)

(52) U.S. Cl. .......................... 600/585; 81/487

(58) Field of Classification Search .............. 600/434, 600/585; 606/1; 604/159; 81/487; 279/42, 279/48
See application file for complete search history.

(56) References Cited

U.S. PATENT DOCUMENTS

| | | | |
|---|---|---|---|
| 4,398,322 A * | 8/1983 | Ewen ............................ 24/595.1 |
| 4,726,369 A * | 2/1988 | Mar ................................... 606/1 |
| 5,137,288 A * | 8/1992 | Starkey et al. .................. 279/42 |
| 5,137,517 A | 8/1992 | Loney et al. |
| 5,161,534 A * | 11/1992 | Berthiaume ................... 600/434 |
| 5,219,332 A | 6/1993 | Nelson et al. |
| 5,325,746 A * | 7/1994 | Anderson ......................... 81/487 |
| 5,325,868 A * | 7/1994 | Kimmelstiel ................... 600/585 |
| 5,392,778 A * | 2/1995 | Horzewski ..................... 600/434 |
| 5,685,730 A * | 11/1997 | Cameron et al. ............... 439/335 |
| 6,030,349 A | 2/2000 | Wilson et al. |
| 2003/0225395 A1 | 12/2003 | Griffis et al. |
| 2004/0215108 A1 | 10/2004 | Windheuser |
| 2005/0070820 A1* | 3/2005 | Boutillette et al. ............. 600/585 |

FOREIGN PATENT DOCUMENTS

| | | |
|---|---|---|
| JP | U 6-17751 | 8/1994 |
| WO | WO 2005/032638 A2 | 4/2005 |

OTHER PUBLICATIONS

International Search Report dated Sep. 28, 2006 for International Application No. PCT/US2006/018419.
Office Action dated Apr. 19, 2011 for Japanese Patent Application No. 2008-511403, with English translation.

* cited by examiner

*Primary Examiner* — Max Hindenburg
*Assistant Examiner* — Adam Eiseman
(74) *Attorney, Agent, or Firm* — Brinks Hofer Gilson & Lione

(57) ABSTRACT

A wire guide torque device includes a handle member having a proximal end and a distal end wherein a groove extends between the proximal end and the distal end of the handle member for inserting a wire guide. A retaining ring is rotatably disposed on the proximal end of the handle member for securing the wire guide inside the groove along the proximal end of the handle member. A lever is slidably disposed in the distal end of the handle member for securing the wire guide inside the groove along the distal end of the handle member. The device further includes a pin having a first end and a second end, wherein the first end is engaged with the lever and the second end is engaged with the handle member.

25 Claims, 7 Drawing Sheets

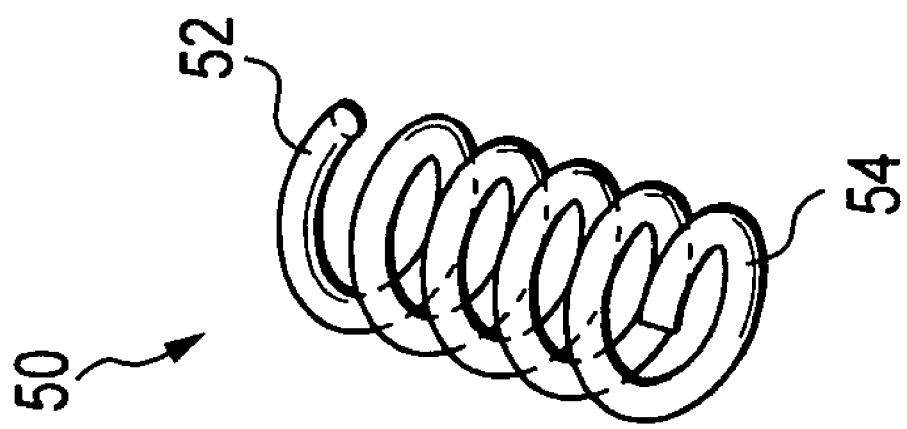

WIRE GUIDE TORQUE DEVICE

RELATED APPLICATIONS

This application claims priority to provisional application No. 60/680,102 filed on May 12, 2005, the entire disclosure of which is incorporated by reference herein.

FIELD OF THE INVENTION

The present invention relates to the field of medical devices, and more particularly to medical devices for grasping and maneuvering wire guides during medical procedures.

BACKGROUND

Wire guides are used during many medical procedures in the gastrointestinal system, including the pancreatobiliary system (i.e., the biliary tree), the stomach, and the esophagus. During vascular procedures, such as balloon angioplasty, stent placement, and endoluminal grafts for aortic aneurysms, the use of wire guides are essential in assessing the site of the particular obstruction in the affected artery. Wire guides are long, slender, relatively flexible wires or wire-like elongate devices that are used to gain and maintain access to the body's narrow passageways during minimally invasive medical procedures. Because of the substantial length of wire guides, using wire guides can be cumbersome and require constant, delicate manipulation during time-sensitive medical procedures.

Wire guides often must be maintained in a stationary position relative to the patient while a physician performs various procedures. In particular, maintaining the wire guide in a stationary position is important to prevent loss of access to a target anatomy, for example, a duct in the biliary tree. Also, during an esophageal dilation, a physician must secure a wire guide within the esophagus and across an esophageal stricture as one or more dilators are advanced over the wire guide. Likewise, during a percutaneous endoscopic gastromy (PEG) tube placement, a wire guide must be secured relative to the patient's mouth, esophagus, and stomach as a physician inserts a feeding tube.

Due to the complexity of these types of procedures, physicians often need to maneuver the wire guide during medical procedures. However, due to the difficulty in grasping the wire guide, the task of positioning and maneuvering the wire guide generally requires the help of an assistant to grip and manipulate the wire during usage. The difficulty associated with positioning and maneuvering the wire guide, however, tends to shift the focus of the assistant from their other areas of responsibility, such as checking the patient, checking monitors for relevant information, or carrying out other tasks.

As a way of simplifying procedures involving wire guides, devices have been developed to assist in the positioning and maneuvering of the wire guide during medical procedures. One such known wire guide device includes a cylindrical body and a slot extending longitudinally for the entire length of the device for side loading of the wire guide therein. The device further includes two biased closed jaws on either side of the slot and two compression handles for opening the jaws. A problem with this device is that when rotating the device for torquing the wire guide, one of the compression handles may be pressed inadvertently. As a result, the jaws may separate and inadvertently release the wire guide. Another problem with this device is that the slot extends the entire length of the device. Thus, during use, the smooth, cylindrical proximal end of the wire guide may slide out from between the jaws and thereby exit the slot of the device.

Another known device includes pin-vise type wire grips that include a structure similar to a drill chuck with a cylindrical handle. The chuck is threaded over the proximal end of the wire guide and advanced to a desired position. A chuck collet, which is a part of the pin-vise, is then rotated to secure the pin-vise to the wire guide and serves as a grip to facilitate manual rotation and advancement of the wire guide. However, use of this type of device can become time consuming and inconvenient because of the length of the wire guide and time associated with threading the device onto the wire guide, as well as the time associated with tightening the chuck collet.

Another known wire guide device utilizes a locking nut portion that locks onto the wire when turned in one direction and releases when turned in the opposite direction thereby requiring the physician to utilize two hands when locking an unlocking the device to the wire guide. Additionally, it may be necessary to completely remove and reinsert the wire guide into this type wire guide device during positioning and maneuvering of the wire guide. As a consequence, maneuvering of the wire guide can become time consuming and distracting to the physician during complicated medical procedures.

What is needed is a wire guide torque device that can quickly and easily engage the wire guide, requires minimal effort to lock and unlock to the wire guide during usage, and allows a physician to operate the device using one hand during positioning and maneuvering of the wire guide. Also, the wire guide torque device should require minimal time and effort to operate during medical procedures.

SUMMARY

In one aspect of the invention, a wire guide torque device is provided that comprises a locking mechanism that engages a wire guide so as to allow the wire guide to be easily advanced for positioning and maneuvering through a vessel during medical procedures. In another aspect of the invention, a wire guide torque device is provided that secures to a wire guide at any location along the length of the wire during medical procedures.

In a preferred embodiment of the present invention, the wire guide torque device is comprised of a handle member having a proximal end and a distal end wherein a groove extends between the proximal end and the distal end of the handle member for inserting a wire guide. A retaining ring is rotatably disposed on the proximal end of the handle member for securing the wire guide inside the groove along the proximal end of the handle member. A lever is slidably disposed in the distal end of the handle member for securing the wire guide inside the groove along the distal end of the handle member. The wire guide torque device also includes a pin for securing the lever to the handle member, the pin having a first end that is engaged with the lever and a second end that is engaged with the handle member.

The wire guide is inserted into the groove of the handle member by aligning the retaining ring with the groove of the handle member and by depressing the lever. Upon insertion of the wire guide into the handle member the wire guide can be advanced along the groove of the handle member. When the lever is depressed, the wire guide is free to be maneuvered along the groove of the handle member to a desired location. When the lever is released, the wire guide is locked into position in the groove of the handle member. The lever presses against the wire guide creating a frictional force between the groove of the handle member and the wire guide that is sufficient to inhibit, limit, and/or prevent the movement of the wire guide along the groove of the handle member.

In another aspect of the present invention, a method of maneuvering a wire guide comprises providing a wire guide torque device comprising a handle member having a proximal end and a distal end wherein a groove extends between the proximal end and the distal end of the handle member for inserting a wire guide. The method also comprises providing a retaining ring rotatably disposed on the proximal end of the handle member for securing the wire guide inside the groove along the proximal end of the handle member and providing a lever slidably disposed in the distal end of the handle member for securing the wire guide inside the groove along the distal end of the handle member. Additionally, the method comprises the steps of rotating the retaining ring to align with the groove of the handle member, depressing the lever to align with the groove of the handle member, and inserting a wire guide inside the groove of the handle member.

BRIEF DESCRIPTION OF THE DRAWINGS

Several embodiments of the present invention will now be described by way of example with reference to the accompanying drawings, in which:

FIG. 19 shows a perspective view of a biasing member of the lever.

DESCRIPTION OF THE INVENTION

Figure 1:
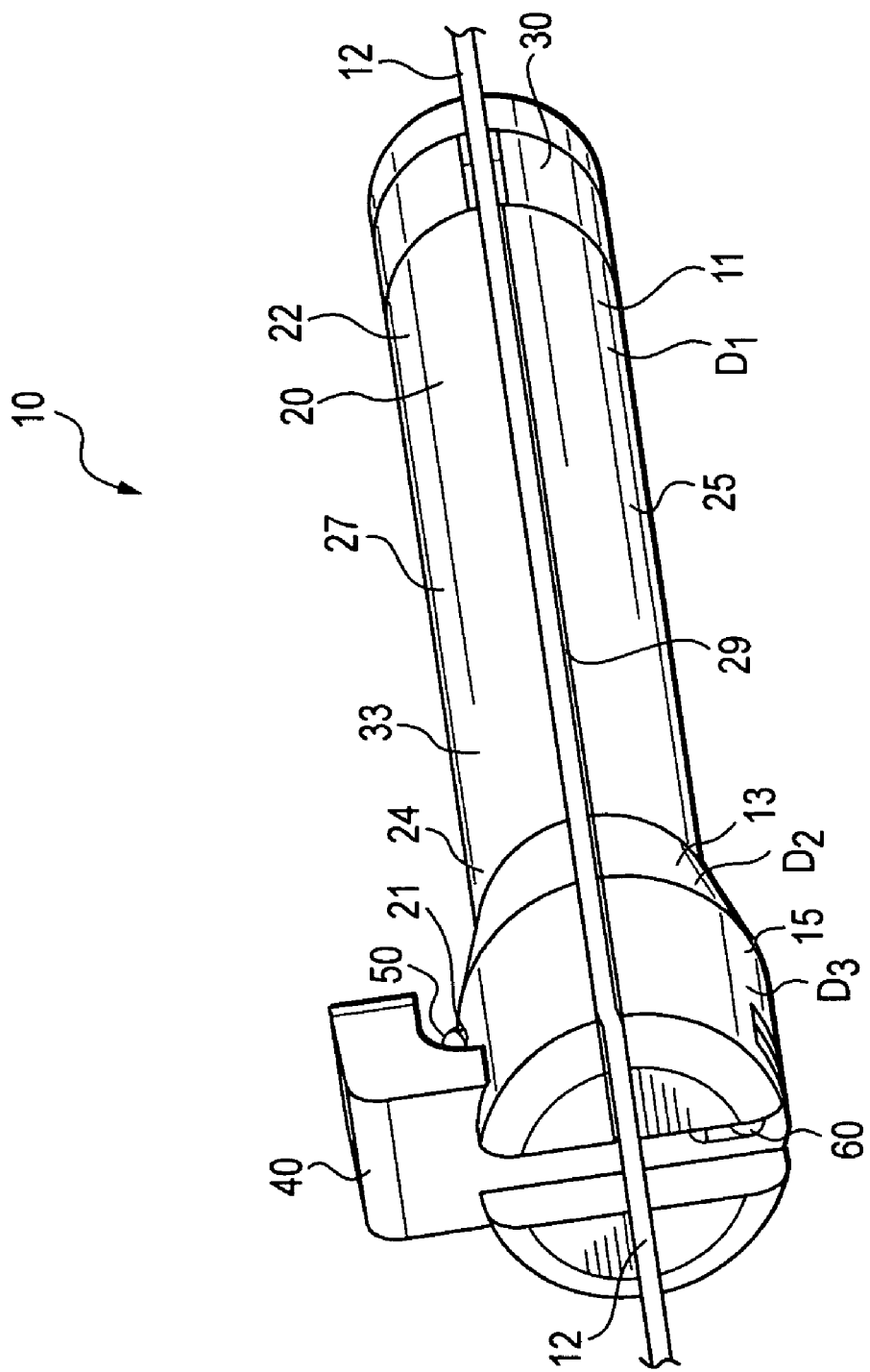
FIG. 1 shows a perspective view of a wire guide torque device.
Figure 3:
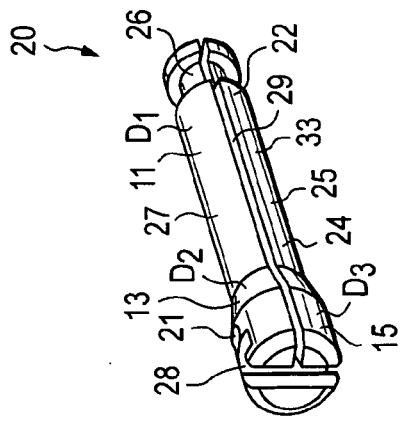
FIG. 3 shows a partial perspective view of the handle member of the wire guide torque device.
Figure 5:
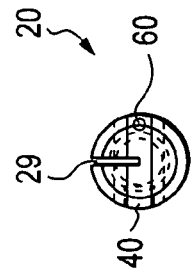
FIG. 5 shows an end view of one end of the handle member of the wire guide torque device.
Figure 2:
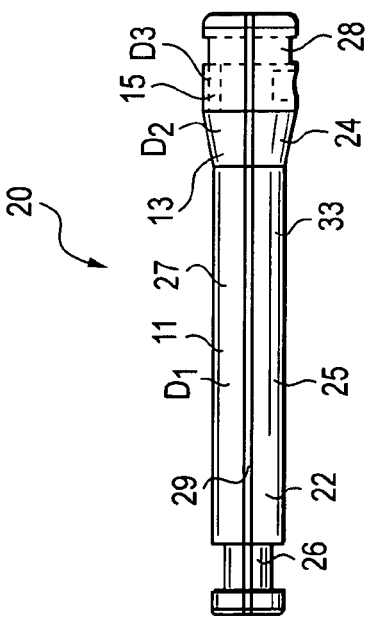
FIG. 2 shows a partial side view of a handle member of the wire guide torque device.
Figure 4:
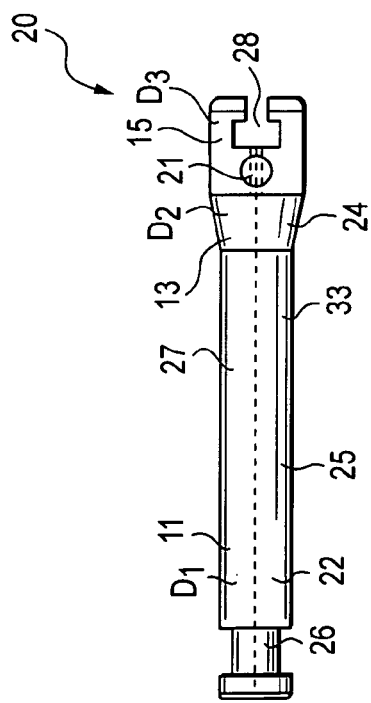
FIG. 4 shows a partial side view of the handle member of the wire guide torque device.
Figure 6:
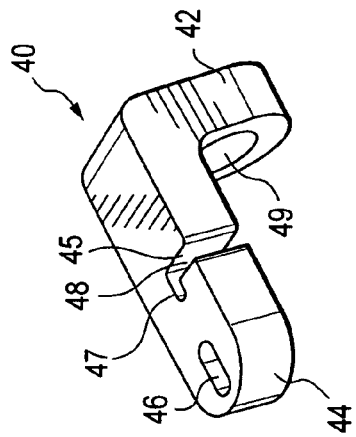
FIG. 6 shows a side view of a first leg of a lever.
Figure 7:
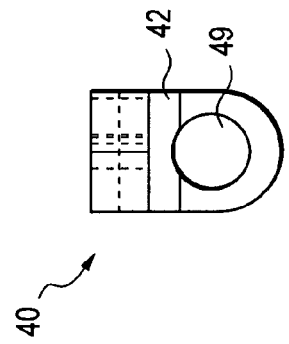
FIG. 7 shows a perspective view of the lever of the wire guide torque device.
Figure 8:
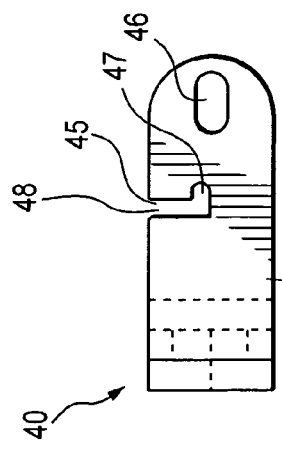
FIG. 8 shows a side view of the lever of the wire guide torque device.
Figure 9:
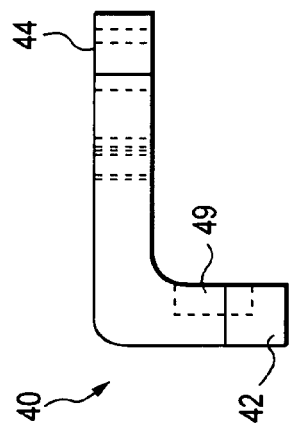
FIG. 9 shows a top view of a second leg of the lever.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale and in certain instances details have been omitted, which are not necessary for an understanding of the present invention, such as conventional fabrication and assembly.

Referring now to FIG. 1, a wire guide torque device 10 of the present invention is shown. A wire guide torque device 10 includes a handle member 20, a retaining ring 30, and a lever 40. The wire guide torque device 10 further includes a biasing member 50, such as spring or similar compressed biasing mechanism, engaged to the lever 40. The wire guide torque device 10 also includes a pin 60 for securing the lever 40 to the handle member 20. The handle member 20 includes a proximal end 22 and a distal end 24 wherein a groove 29 extends between the proximal end 22 and the distal end 24 of the handle member 20 for inserting a wire guide 12. The retaining ring 30 is rotatably disposed on the proximal end 22 of the handle member 20 for securing the wire guide 12 inside the groove 29 along the proximal end 22 of the handle member 20. The lever 40 is slidably disposed in the distal end 24 of the handle member 20 for securing the wire guide 12 inside the groove 29 along the distal end 24 of the handle member 20.

The wire guide torque device 10 is configured to receive and hold the wire guide 12, or similar type of elongate medical device (hereinafter collectively referred to as a "wire guide"). The wire guide 12 is inserted into the groove 29 of the wire guide torque device 10 and extends along the length of the handle member 20. The wire guide 12 can be inserted into the wire guide torque device 10 at any point along the body of the wire guide 12 by simply passing the wire guide 12 laterally into or through the groove 29 of the handle member 20, thereby eliminating the need to longitudinally insert an end of the wire guide 12 into the groove 29 to engage the wire guide 12 to the device 10. The ability of the wire guide 12 to be introduced at any point during a medical procedure reduces the associated time of the medical procedure.

In the embodiment illustrated in FIGS. 2-5, the handle member 20 of the wire guide torque device 10 is elongate and has a cylindrical shape. However, the shape of the handle member 20 can include other shapes, such as rectangular, elliptical, square, or any combination thereof. The optimal length of the handle member 20 is determined by considering factors such as design and material used, as well by what is determined through experimentation to work best. The proximal end 22 of the handle member 20 includes a proximal channel 26 for receiving the retaining ring 30 (FIGS. 12-15). The distal end 24 of the handle member 20 includes a distal channel 28 for receiving the lever 40 (FIGS. 6-9). The handle member 20 may include a bottom surface 25 and a top surface 27, wherein the top surface 27 provides an opening 21 to receive the biasing member 50 (FIG. 19) engaged between the handle member 20 and the lever 40.

The groove 29 of the handle member 20 generally defines a cavity extending along the entire length of the handle member 20. The groove 29 can include a width that is greater than the typical width of a typical wire guide. The groove 29 secures the wire guide 12 along the path of the handle member 20. The groove 29 is configured and oriented so as to prevent the wire guide 12 from unintentionally sliding out of the handle member 20. When the wire guide 12 is inserted laterally into or through the groove 29, the cavity preferably provides a frictional engagement by pressing against the wire guide 12 to prevent the flexible wire guide 12 from inadvertently slipping out of the groove 29. However, the friction provided by the groove 29 should not be so great as to prevent or inhibit relatively easy insertion or withdrawal of the wire guide 12 from the groove 29 of the handle member 20.

In the embodiment illustrated, the handle member 20 (FIG. 2) can include a first portion 11 comprising a first diameter D1, a second portion 13 comprising a second diameter D2, and a third portion 15 comprising a third diameter D3. The first diameter D1 may be smaller than the second diameter D2. Additionally, the second diameter D2 may be smaller than the third diameter D3. In the embodiment illustrated, the second diameter D2 varies and provides a transition between the first diameter D1 and the third diameter D3. The varying diameter of the handle member 20 enables a physician to easily grip and operate the device with one hand during positioning and maneuvering of the wire guide 12. The third portion 15 of the handle member 20 is sized and configured to align with the index finger of the user while adjusting the lever 40 of the handle member 20. Preferably, the size of the varying diameters D1, D2, D3 of the handle member 20 should be sufficient to facilitate the maneuvering of the wire guide or similar medical device. A skilled artisan would appreciate that other designs utilizing different diameter combinations are within the scope of the present invention. For example, in an alternative embodiment, the handle member 20 can include a uniform diameter, such as a first diameter D1, along the entire length of the handle member 20.

The handle member 20 may be preferably formed of molded plastic material. Alternatively, the handle member 20 and other component parts of the device 10, such as the retaining ring 30, lever 40, pin 60, and biasing member 50 may be formed of any other suitable material, including metal, stainless steel and nitinol. The component parts of the wire guide torque device 10 are preferably formed of a material which may be repeatedly sterilized by medical providers for re-use during medical procedures. Alternatively, the wire guide torque device 10 may be initially sterilized following use and then disposed of.

Figure 10:
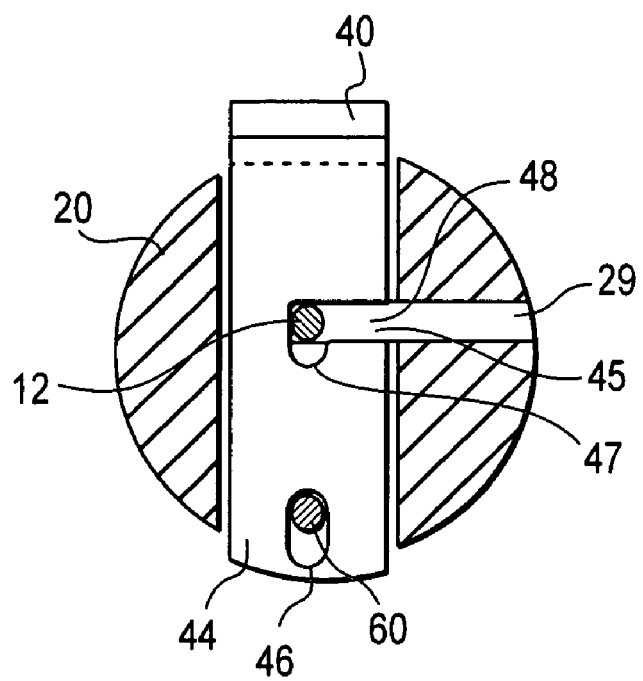
FIG. 10 shows a partial cross-sectional view of the lever in a depressed configuration.
Figure 11:
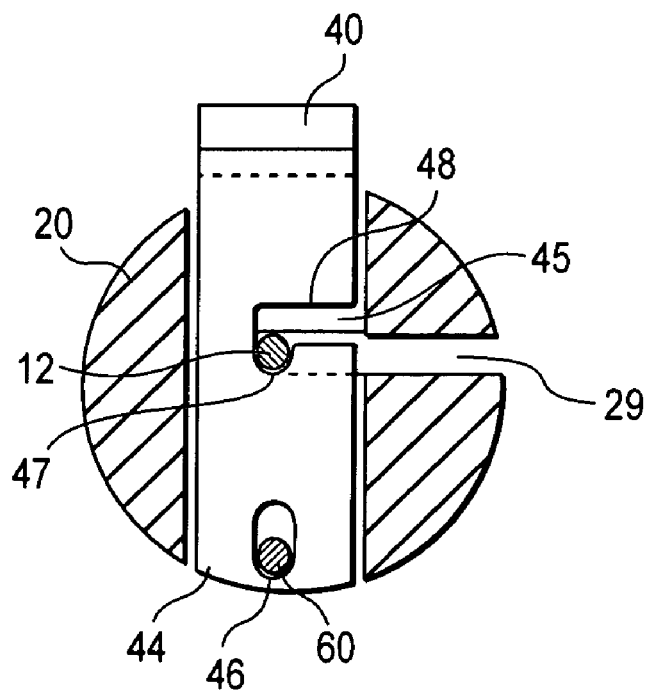
FIG. 11 shows a partial cross-sectional view of the lever in a released configuration.
Figure 13:
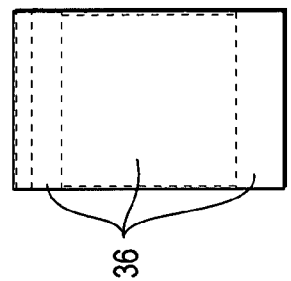
FIG. 13 shows a perspective view of the retaining ring of the wire guide torque device.
Figure 15:
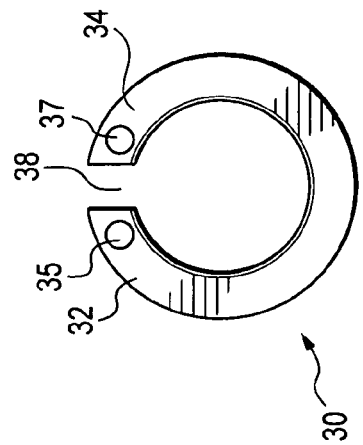
FIG. 15 shows a sectional view of the gripping surface of the retaining ring of the wire guide torque device.
Figure 12:
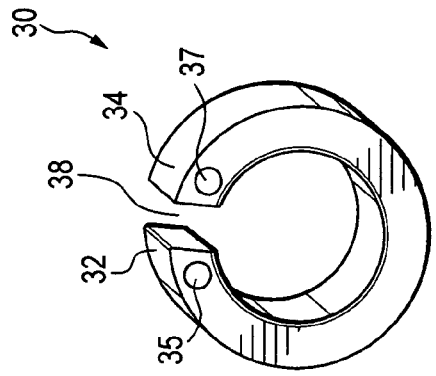
FIG. 12 shows a sectional view of a gripping surface of a retaining ring.
Figure 14:
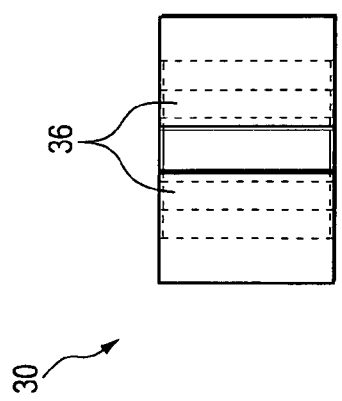
FIG. 14 shows a side view of the retaining ring of the wire guide torque device.

FIGS. 6-9 illustrate the lever 40 of the wire guide torque device 10. As illustrated, the lever 40 preferably includes a first leg 44 and a second leg 42. The second leg 42 has an opening 49 for receiving the biasing member 50 (FIG. 19) for engaging the lever 40 relative to the handle member 20. The biasing member 50 (FIG. 19) includes a first end 52 and second end 54 wherein the first end 52 is in contact with the lever 40 and the second end 54 is in contact with the handle member 20. The first leg 44 has an L-shaped groove 48 that is disposed along the midpoint of the first leg 44. The first leg 44 also includes a slot 46 at a distal end of the first leg 44. The L-shaped groove 48 comprises an entry leg 45 and a locking leg 47. As will be explained in greater detail below, the entry leg 45 may be aligned with the groove 29 of the handle member 20 to permit insertion or removal of the wire guide 12. The locking leg 47 is utilized to secure the wire guide 12 against movement relative to the handle member 20 (FIGS. 10-11). The pin 60 (FIGS. 16-18) includes a first end 62 and a second end 64 wherein the first end 62 is engaged with the slot 46 of the first leg 44 of the lever 40 and the second end 64 is engaged with a slot located on the handle member 20 (shown in FIGS. 10 and 11 with the pin 60 extending between the lever 40 and the handle 20).

When the lever 40 is depressed the entry leg 45 of the L-shaped groove 48 is aligned with the groove 29 of the handle member 20 (FIG. 10). With the entry leg 45 of the L-shaped groove 48 being aligned with the groove 29 of the handle member 20, the wire guide 12 can be inserted into the groove 48 and maneuvered into position. As will be explained in greater detail below, when the lever 40 is released (FIG. 11), the biasing member 50 pushes the lever 40 outward to bind the wire guide 12 between an interior surface of the locking leg 47 of the L-shaped groove 48 and an interior surface of the handle member 20. The pin 60, which is disposed in slot 46, prevents the lever 40 from being completely removed from the handle member 20. The lever 40 allows the physician to quickly remove the wire guide 12 from the wire guide torque device 10 by simply depressing the lever 40 and sliding the wire guide 12 from the groove 29. Additionally, a physician is able to quickly reinsert another wire guide or reposition the device 10 along the current wire guide 12 without removing the wire guide torque device 10.

In a preferred embodiment, the lever 40 operates as a locking mechanism to secure the wire guide 12 in the groove 29 of the handle member 20. The biasing member 50, such as spring, curvilinear strut, or similar compressed mechanism, engages the lever 40 such that the lever 40 moves between a depressed configuration and a released configuration. When the lever 40 is fully depressed, the wire guide 12 can be removed or inserted in the groove 29 of the handle member 20 (FIG. 10). When the lever 40 is partially depressed, the wire guide 12 is free to be maneuvered longitudinally along or rotationally within the groove 29 to any desired location. When the lever 40 is released, the wire guide 12 is locked into position in the groove 29 of the handle member 20 (FIG. 11). The lever 40 presses against the wire guide 12 to create a frictional force between the groove 29 of the handle member 20 and the wire guide 12 that is sufficient to inhibit, limit, and/or prevent the movement of the wire guide 12 along the groove 29 of the handle member 20. However, the wire guide 12 is not damaged by the wire guide torque device 10. In particular, this configuration avoids damage to the wire guide 12, such as stripping, which can result from locking the wire guide 12 within a wedge or v-shaped slot as in other devices.

FIGS. 12-15 illustrate a retaining ring 30 having a first end 32 and a second end 34 forming a C-shape defining a gap portion 38 positioned between the first end 32 and second end 34 of the retaining ring 30. The retaining ring 30 can include slots 35, 37 positioned on the first end 32 and second end 34 of the retaining ring 30, respectively. The slots 35, 37 can engage nubs on the handle member 20 to provide a tactile feel and maintain the retaining ring 30 in an alignment position. The retaining ring 30 is rotatably coupled to the proximal channel 26 of the handle member 20. The gap portion 38 of the retaining ring 30 provides an opening for inserting the wire guide 12 into the groove 29 of the handle member 20. When the retaining ring 30 is rotated about the handle member 20 to an open position wherein the gap portion 38 is aligned with the groove 29, the wire guide 12 can be inserted or removed from the groove 29 of the handle member 20. Conversely, when the retaining ring 30 is rotated about the handle member 20 to a closed position wherein the gap portion 38 is misaligned with the groove 29, the wire guide 12 is prevented from being removed from the groove 29 of the handle member 20. The retaining ring 30 of the wire guide torque device 10 allows the wire guide 12 to be quickly inserted and removed from the device at any location along the wire guide 12 during medical procedures.

The retaining ring 30 includes a gripping surface 36 for providing torque when rotating the retaining ring 30 about the axis of the handle member 20. Additionally, the gripping surface 36 can be provided along the surface of the handle member 20 to allow the user to properly grip the handle member 20 and apply torque during manipulation and repositioning of the wire guide 12 during medical procedures. The gripping surface 36 further provides a frictional surface for grasping the device 10 during medical procedures wherein the device may be exposed to bodily fluids. In another embodiment, the wire torque guide device 10 can include at least two retaining rings 30 for securing the wire guide 12 wherein the second retaining ring is positioned along the length of the handle member 20. In an alternate embodiment of the present invention, the retaining ring 30 can comprise a length that extends along a substantial portion of the handle member 20. The length of the retaining ring 30 may vary depending on the shape and particular design of the wire guide device 10 and fall within the scope of the present invention. For example, instead of including a retaining ring 30 having a ring shape disposed along the proximal end 22 of the handle member 20, the retaining ring 30 can include a spherical shape, such as a sleeve, extending between the proximal end 22 and distal end 24 of the handle member 20, or any portion thereof.

Figure 17:
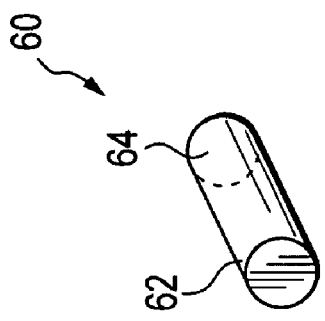
FIG. 17 shows a perspective view of the pin of the wire guide torque device.
Figure 18:
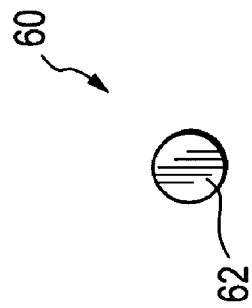
FIG. 18 shows an end view of an end of the pin of the wire guide torque device.
Figure 16:
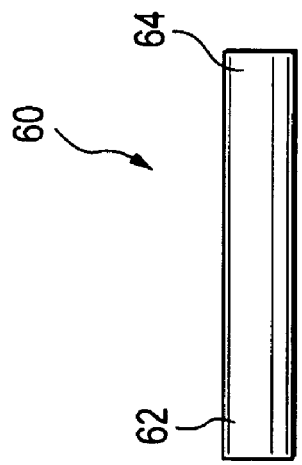
FIG. 16 shows a side view of a pin of the wire guide torque device.

FIGS. 16-18 illustrate the pin 60 for securing the lever 40 to the handle member 20. The pin 60 preferably has a cylindrical shape for engaging the slot of the handle member 20. In other embodiments, the pin 60 can include other shapes, such as rectangular, elliptical, square, or any combination thereof. FIG. 19 illustrates the biasing member 50, which engages the lever 40 thereby allowing the lever 40 to revert to a released position after being partially or fully depressed.

The wire guide torque device 10 may also comprise a coating 33 (see FIG. 1) to facilitate grasping and maneuvering of the wire guide torque device 10 during a medical procedure. The coating 33 may be applied to the entire composite structure of the wire guide torque device 10 or singly to specific components, such as the handle member 20, retaining ring 30, lever 40 or any combination thereof. The coating may be applied by dipping, molding, or spraying a suitable material, such as polytetraflouroethylene, urethane, and/or other polymeric coatings, directly to the wire guide torque device 10.

The coating 33 may be applied by heat shrinking a heat shrinkable material about the desired portions of the wire guide torque device 10. In preferred embodiments, the thickness of the coating 33 is between approximately 2.5 micrometers and 2.5 millimeters. In some embodiments, the thickness of the coating 33 is between approximately 2.5 micrometers and 100 micrometers. In other embodiments, the thickness of the coating 33 can be between approximately 2.5 micrometers and 50 micrometers. These preferred thicknesses provide suitable coatings while not adding significantly to the overall thickness of the device 10. One of ordinary skill in the art would appreciate that the amount and thickness of the coating 33 is related to the length, width and material of the coating 33. Additionally, a wire guide torque device 10 without a coating 33 is within the scope of the present invention.

The above figures and disclosures are intended to be illustrative and not exhaustive. This description will suggest many variations and alternatives to one of ordinary skill in the art. All such variations and alternatives are intended to be encompassed within the scope of the attached claims. Those familiar with the art may recognized other equivalents to the specific embodiments described herein which equivalents are also intended to encompass by the attached claims. Moreover, the use of this invention on a wire guide is not a limitation of the claims. Use of this device with other tubing and elongate medical devices used in medical procedures and the like is understood to be within the scope of the claims.

The invention claimed is:

1. A wire guide torque device, comprising:
   a handle member having a proximal end and a distal end wherein a groove extends between the proximal end and the distal end of the handle member for inserting a wire guide;
   a retaining ring rotatably disposed on the proximal end of the handle member at a proximal end position and configured to be rotatably maintained within a proximal channel and the retaining ring rotatable about an axis at the proximal end position from an open position to a closed position, the closed position configured for laterally securing the wire guide inside the groove along the proximal end of the handle member; and
   a lever slidably disposed in the distal end of the handle member, the lever configured for longitudinally securing the wire guide inside the groove along the distal end of the handle member relative to the handle member.

2. The wire guide torque device of claim 1 further comprising a biasing member having a first end and second end wherein the first end is in contact with the lever and the second end is in contact with the handle member.

3. The wire guide torque device of claim 1 further comprising a pin having a first end engaged with the lever and a second end engaged with the handle member wherein the pin limits lateral movement of the lever relative to the handle member.

4. The wire guide torque device of claim 1 wherein the lever includes an L-shaped groove having a first leg and a second leg for receiving the wire guide, wherein the first leg is aligned with the groove of the handle member when the lever is depressed.

5. The wire guide torque device of claim 4 wherein when the lever is released, the lever binds the wire guide between an end of the second leg of the L-shaped groove and an interior surface of the handle member.

6. The wire guide torque device of claim 4 wherein the wire guide is inserted into the groove of the handle member by aligning the retaining ring with the groove of the handle member.

7. The wire guide torque device of claim 1 wherein the retaining ring includes a first end and a second end forming a C-shape having a gap portion positioned between the first end and second end of the retaining ring, wherein the gap portion comprises a first position wherein the gap portion is aligned with the groove to allow the wire guide to be inserted into the groove of the handle member and a second position wherein the gap portion is misaligned with the groove to prevent the wire guide from being removed from the groove of the handle member.

8. The wire guide torque device of claim 1 wherein the handle member includes a first portion having a first diameter, a second portion having a second diameter, and a third portion having a third diameter wherein the first diameter is smaller than the second diameter and the third diameter.

9. The wire guide torque device of claim 8 further comprising a wire guide disposed inside the groove of the handle member.

10. The wire guide torque device of claim 1 wherein the lever comprises a released position for longitudinally securing the wire guide in relation to the handle member.

11. The wire guide torque device of claim 1 where in the lever comprises a fully depressed position configured to receive or release the wire guide into or from the groove.

12. The wire guide torque device of claim 1 wherein the lever comprises a partially depressed position configured to maneuver the wire guide longitudinally along or rotationally within the groove of the handle member and configured to laterally secure the wire guide in the groove.

13. The wire guide torque device of claim 1 wherein the lever comprises a first portion, the first portion configured to receive a portion of the wire guide therethrough and the first portion configured to move in a direction perpendicular to a direction of movement of the wire guide in the handle.

14. A method of maneuvering a wire guide, the method comprising the steps of:
providing a wire guide torque device comprising a handle member having a proximal end and a distal end wherein a groove extends between the proximal end and the distal end of the handle member for inserting a wire guide;
providing a retaining ring rotatably disposed on the proximal end of the handle member at a proximal end position and configured to be rotatably maintained within a proximal channel and the retaining ring rotatable about the proximal end position from an open position to a closed position, the closed position configured for laterally securing the wire guide inside the groove along the proximal end of the handle member, the retaining ring comprising a gap portion; and
providing a lever slidably disposed in the distal end of the handle member, the lever configured for longitudinally securing the wire guide inside the groove along the distal end of the handle member, the lever comprising an opening;
rotating the retaining ring about an axis at the proximal end position to align the gap portion with the groove on the handle member;
depressing the lever to align the opening with the groove of the handle member; and
inserting a wire guide into the groove of the handle member.

15. The method of claim 14 further comprising the step of releasing the lever to frictionally engage the wire guide between the opening of the lever and the groove of the handle member to longitudinally secure the wire guide relative to the handle member.

16. The method of claim 14, further comprising the step of rotating the retaining ring to misalign the gap portion with the groove of the handle member to laterally secure the wire guide in the groove.

17. A wire guide torque device, comprising:
a handle member having a proximal end, a distal end and a groove extending between the proximal end and the distal end of the handle member, the groove configured to laterally receive a wire guide;
a first retaining member rotatably coupled to a proximal channel on the proximal end of the handle member, the first retaining member configured to be rotatably maintained within the proximal channel and to laterally secure the wire guide inside the groove along the proximal end of the handle member, the retaining ring rotatable about an axis at the proximal end position from an open position to a closed position, the closed position configured for laterally securing the wire guide inside the groove along the proximal end of the handle member;
a second retaining member slidably disposed on the distal end of the handle member, the second retaining member configured to longitudinally secure the wire guide in relation to the handle member.

18. The wire guide torque device of claim 17, wherein the second retaining member further comprises a fully depressed position configured to laterally receive or release the wire guide into or from the groove.

19. The wire guide torque device of claim 17, wherein the device further comprises a coating.

20. The wire guide torque device of claim 17, wherein the second retaining member is configured to laterally secure the wire guide inside the groove along the distal end of the handle member in a partially depressed position and configured to longitudinally secure the wire guide in relation to the handle member in a released position.

21. The wire guide torque device of claim 17 further comprising a pin having a first end engaged with the second retaining member and a second end engaged with the handle member wherein the pin limits lateral movement of the second retaining member relative to the handle member.

22. The wire guide torque device of claim 17 wherein the second retaining member includes an L-shaped groove having a first leg and a second leg for receiving the wire guide, wherein the first leg is aligned with the groove of the handle member when the second retaining member is depressed.

23. The wire guide torque device of claim 22 wherein when the second retaining member is released, the second retaining member binds the wire guide between an end of the second leg of the L-shaped groove and an interior surface of the handle member.

24. The wire guide torque device of claim 17 wherein the first retaining member includes a first end and a second end forming a C-shape having a gap portion positioned between the first end and second end of the first retaining member.

25. The wire guide torque device of claim 17 further comprising a wire guide disposed in the groove of the handle member.

* * * * *